United States Patent

Fujimoto et al.

[11] 4,021,449
[45] May 3, 1977

[54] DERIVATIVES OF MITOMYCIN C

[75] Inventors: Yasuo Fujimoto, Tokyo; Kinichi Nakano; Chikahiro Urakawa, both of Machida, all of Japan

[73] Assignee: Kyowa Hakko Kogyo Co., Ltd., Japan

[22] Filed: Dec. 16, 1974

[21] Appl. No.: 532,922

[30] Foreign Application Priority Data

Dec. 17, 1973 Japan .............................. 48-139579

[52] U.S. Cl. ............................ 260/326.24; 424/274
[51] Int. Cl.$^2$ ...................................... C07D 209/56
[58] Field of Search .............................. 260/326.24

[56] References Cited

UNITED STATES PATENTS

| | | | |
|---|---|---|---|
| 3,450,705 | 6/1969 | Matsui et al. | 260/326.24 |
| 3,506,681 | 4/1970 | Matsui et al. | 260/326.24 |
| 3,514,452 | 5/1970 | Matsui et al. | 260/326.24 |

FOREIGN PATENTS OR APPLICATIONS

| | | | |
|---|---|---|---|
| 2,459,616 | 6/1975 | Germany | 260/326.24 |
| 4,018,117 | 8/1965 | Japan | 260/326.24 |

Primary Examiner—Ethel G. Love
Attorney, Agent, or Firm—Craig & Antonelli

[57] ABSTRACT

1a-Higher aliphatic acyl derivatives of mitomycin C have been found to have superior anti-tumor activity and lipid-solubility as compared with known 1a-acyl derivatives of mitomycin C. Also, the new derivatives exhibit far lower toxicity than mitomycin C. These derivatives are represented by the following formula:

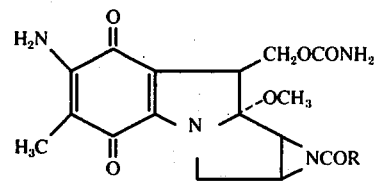

wherein R is an aliphatic hydrocarbon group having 9–29 carbon atoms or a group wherein a hydrogen atom of the aliphatic hydrocarbon group is substituted by a hydroxy group.

4 Claims, 11 Drawing Figures

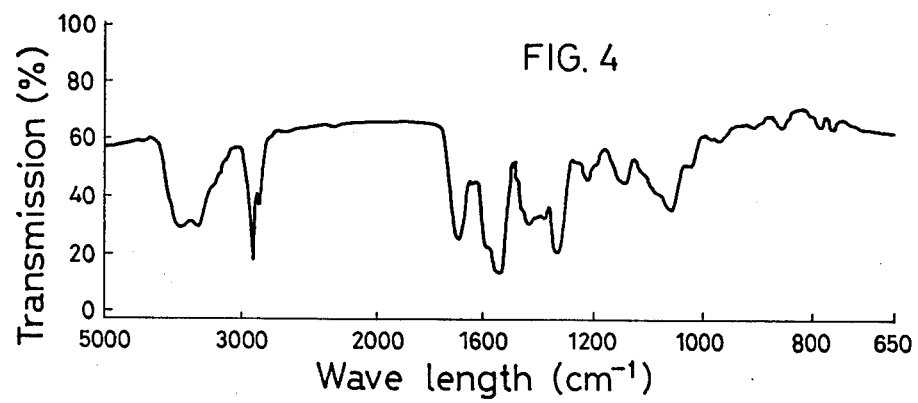
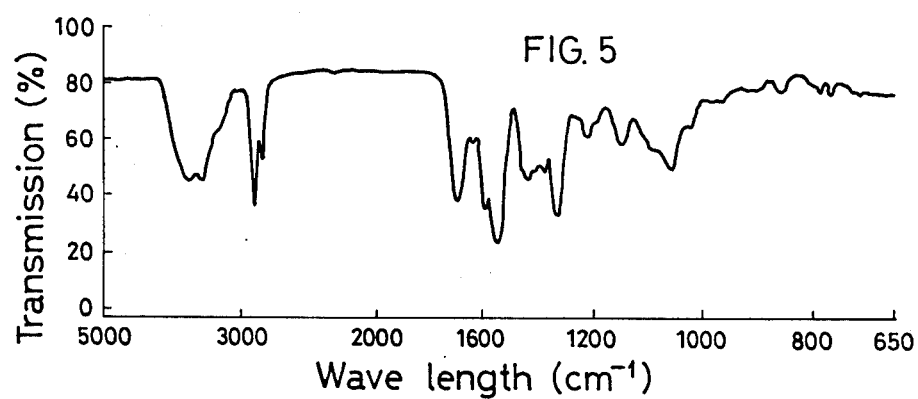
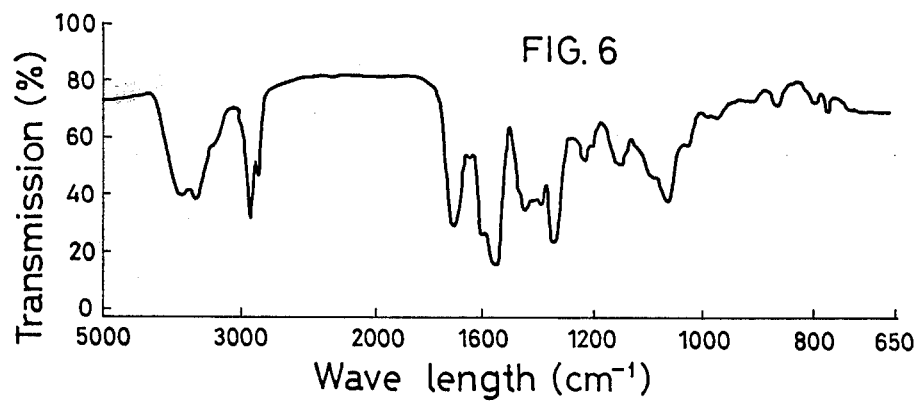

DERIVATIVES OF MITOMYCIN C

BACKGROUND OF THE INVENTION

This invention relates to new derivatives of mitomycin C.

The new derivatives of mitomycin C contemplated by the present invention are 1a-higher aliphatic acyl derivatives of mitomycin C having the general formula:

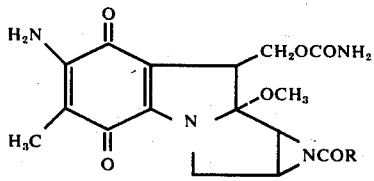

wherein R is an aliphatic saturated or ethylenically unsaturated hydrocarbon group having 9–29 carbon atoms, preferably, 9–21 carbon atoms or a group wherein a hydrogen atom of said aliphatic hydrocarbon group is substituted by a hydroxy group.

Mitomycin C is a compound which is well known to have a very strong antibacterial activity against Gram-nagative and Gram-positive bacteria. The compound is also well known, particularly, to have a remarkably strong anti-tumor activity. However, because mitomycin C at the same time is very toxic, there have heretofore been proposed various derivatives of mitomycin C which have less toxicity. For example, U.S. Pat. No. 3,514,452 discloses 1a-lower aliphatic acyl derivatives, such as 1a-acetyl and 1a-butyryl derivatives of mitomycin C. These compounds have much less toxicity than mitomycin C.

However, these 1a-lower aliphatic acyl derivatives of mitomycin C are not satisfactory in respect of the anti-tumor activity and the lipid-solubility and, therefore, an improvement is still desired.

SUMMARY OF THE INVENTION

The 1a-higher aliphatic acyl derivatives of mitomycin C of the present invention are found to have superior anti-tumor activity against Sarcoma 180 solid tumor in mice and lipid-solubility as compared with those of the known 1a-acyl derivatives of mitomycin C. Moreover, the new derivatives of mitomycin C of the invention exhibit far lower toxicity than mitomycin C.

DESCRIPTION OF THE INVENTION

In accordance with the present invention, the new 1a-higher aliphatic acyl derivatives of mitomycin C are prepared by acylating mitomycin C having the formula:

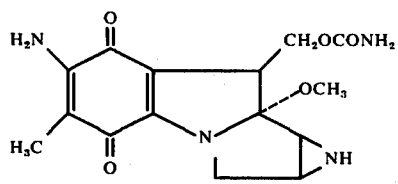

with a higher aliphatic acylating agent. This acylating agent may be a higher fatty acid, a higher fatty acid anhydride, a higher fatty acid halide, an active ester of a higher fatty acid or a higher fatty acid azide. According to the present invention, the acylation reaction may be carried out by any of the conventional methods usually used for acylation in peptide synthesis.

More specifically, the new derivative of mitomycin C may be prepared, for example, by:

I. reacting mitomycin C with a higher fatty acid in the presence of a dehydrating and condensing agent usually used in peptide synthesis, e.g. a carbodiimide;

II. reacting mitomycin C with a higher fatty acid anhydride or a higher fatty acid halide in the presence of a base; or III. reacting mitomycin C with (a) an active ester of a higher fatty acid, or (b) a higher fatty acid azide, Now, each of the above methods is described in detail below.

In method I, mitomycin C is reacted with a higher fatty acid represented by the formula: RCOOH (wherein R is an aliphatic hydrocarbon group having 9 to 29 carbon atoms, preferably 9 to 21 carbon atoms or a group wherein a hydrogen atom of said hydrocarbon group is substituted by a hydroxy group) in the presence of a dehydrating and condensing agent. Reaction is carried out in an inert solvent at $-50°$ C. to $70°$ C., preferably, at $-10°$ C. to $30°$ C. for several minutes to 50 hours, preferably, for 30 minutes to 30 hours. There is no particular restriction in respect of the amount of the higher fatty acid and the dehydrating and condensing agent to be employed. However, it is preferable to use the fatty acid and the dehydrating and condensing agent in more than equimolar amounts based on the amount of mitomycin C.

The examples of suitable higher fatty acid are decanoic acid, undecanoic acid, 10-undecenic acid, lauric acid, tridecanoic acid, 2-tridecenic acid, myristic acid, trans-2-tetradecenic acid, penta-decanoic acid, palmitic acid, hepta-decanoic acid, stearic acid, hydroxy-stearic acid, isostearic acid, linolenic acid, linoleic acid, oleic acid, ricinoleic acid, vaccenic acid, elaidic acid, nonadecanoic acid, arachidic acid, behenic acid, lignoceric acid, erucic acid, trans-1,3-decosenoic acid, montanic acid and melissic acid.

The examples of suitable dehydrating and condensing agents are carbodiimides such as dicyclohexyl-carbodiimide, ditolyl-carbodiimide, pentamethylenekete-cyclo-hexylcarbodiimide, N-cyclohexyl-N'-(morpholinoethyl) carbodiimide, N-cyclohexyl-N'-(diethylaminocyclohexyl) carbodiimide, diisopropyl-carbodiimide, di-n-propyl-carbodiimide, and diphenylketene-p-toluylimide; N,N-dialkylcyanamides such as N,N-dimethylcyanamide and N,N-diethylcyanamide; alkoxyacetylenes such as ethoxyacetylene and isopropoxyacethylene and α-chlorovinylether and tetraethyl phosphite.

As the inert solvent, solvents usually employed in peptide synthesis using such dehydrating and condensing agents as above may be employed. The examples thereof are water; halogenated lower aliphatic hydrocarbons such as chloroform, ethylene-dichloride, methylenechloride, tetrachloroethane and trichloroethylene; lower alkyl esters of lower fatty acids such as ethyl acetate, isopropyl acetate, butyl acetate and ethylpropionate; alcohols such as methanol, ethanol, isopropanol and t-butanol; di-lower alkyl lower fatty acid amides such as dimethylformamide and diethylformamide; ketones such as acetone and methyl ethyl ketone; aromatic hydrocarbons such as benzene, toluene and xylene; lower aliphatic or lower alicyclic ethers such as tetrahydrofuran, dioxane and ethylether; heterocyclic compounds such as pyridine, pyrazine and furane; and nitriles such as acetonitrile, propionitrile and butyronitrile.

In method II, mitomycin C is reacted with a higher fatty acid anhydride represented by the formula: $(RCO)_2O$ (wherein R has the same meaning as defined above) or a higher fatty acid halide represented by the formula: RCOX (wherein R has the same meaning as defined above and X is a halogen atom such as Cl, Br and I) in the presence of a base.

Reaction is carried out in an inert solvent at −50° C. to 70° C., preferably, −10° C. to 30° C. for several minutes to 50 hours, preferably for 30 minutes to 30 hours. Preferably, the higher fatty acid anhydride or higher fatty acid halide is employed in more than equimolar amounts based on the amount of mitomycin C. Further, it is preferable to use more than an equimolar amount of the based on the amount of the higher fatty acid halide or anhydride.

As the higher fatty acid anhydride to be used in method II, anhydrides of the above-mentioned higher fatty acids are suitable for purposes of this invention. Further, as the higher fatty acid halide to be employed, chlorides and bromides of the above-mentioned higher fatty acids are suitable.

The examples of a suitable base are tertiary amines such as triethylamine, trimethylamine, tripropylamine, dimethylaniline and diethylaniline; heterocyclic compounds such as pyridine, and pyrimidine; hydroxides of alkali metal or alkaline earth metal such as sodium hydroxide, potassium hydroxide calcium hydroxide, carbonates or bicarbonates of alkali metal or alkaline earth metal such as potassium carbonate and sodium hydrogencarbonate; and anion exchange resin such as Dowex 1 (trade name for a strongly basic anion exchange resin, produced by the Dow Chemical Co., U.S.A.), Amberlite IRA-400 (trade name for a strongly basic anion exchange resin, produced by Rohm & Haas Co., U.S.A.).

The inert solvent used in method II includes halogenated lower aliphatic hydrocarbons such as chloroform, ethylene-dichloride, methylenechloride, tetrachloroethane and trichloroethylene; lower alkyl esters of lower aliphatic acids such as ethylacetate, isopropyl acetate, butyl acetate and ethylpropionate; di-lower alkyl lower aliphatic amides such as dimethylformamide and diethylformamide; ketones such as acetone and methyl ethyl ketone; aromatic hydrocarbons such as benzene, toluene and xylene; lower aliphatic or lower alicyclic ethers such as tetrahydrofuran, dioxane and ethylether; heterocyclic compounds such as pyridine, pyrazine and furan and nitriles such as acetonitrile, propionitrile and butyronitrile.

Further, when the new derivatives of mitomycin C of the present invention are prepared by method III, mitomycin C is reacted with (a) an active ester of a higher fatty acid represented by the formula: RCOOR' (wherein R has the same meaning as defined above and R' is a residue of an active ester used in peptide synthesis), or (b) a higher fatty acid azide represented by the Formula: $RCON_3$ (wherein R has the same meaning as defined above).

Reaction in method III is carried out in an inert solvent at −50° C. to 70° C., preferably at −10° C. to 30° C. for several minutes to 50 hours, preferably, for 30 minutes to 30 hours. Preferably, more than equimolar amount of the active ester of higher fatty acid or higher fatty acid azide is used based on the amount of mitomycin C.

As suitable examples of the active ester group R' of the active ester of the higher fatty acid, a p-nitrophenyl group, a penta-chlorophenyl group and a methoxymethyl group are mentioned.

As the higher fatty acid portion of the active ester of higher fatty acid or the higher fatty acid azide used in method III, such higher fatty acids as those described with reference to method I may be employed.

Any of the inert solvents mentioned in connection with method II above may be used.

In any of the above methods I, II and III, after the completion of reaction, the reaction mixture is concentrated, if necessary, after carrying out filtration and the concentrate is subjected to extraction with, for example, ethyl acetate and chloroform. Thereafter, the extract is purified by conventional methods such as silica gel chromatography.

In this manner, the desire 1a-higher aliphatic acyl derivatives of mitomycin C are obtained.

Table 1 shows antibacterial spectrum and acute toxicity of various 1a-acyl derivatives of mitomycin C of the present invention.

The acute toxicity (determined as $LD_{50}$) is determined in mice by intraperitoneal injection.

TABLE 1

Antibacterial Spectra and Acute toxicity of 1a-acyl derivatives of mitomycin C of the present invention.

| | Minimum Inhibitory Concentration (µg/ml) | | | Acute toxicity $LD_{50}$ mg/kg |
|---|---|---|---|---|
| | Streptococcus faecalis ATCC 10541 | Staphylococcus aureus ATCC 6538P | Klebsiella penumoniae ATCC 10031 | |
| mitomycin C | 0.391 | 0.049 | <0.025 | 9.0 |
| 1a-acetyl mitomycin C | 6.25 | 1.563 | 0.782 | 23.0 |
| 1a-butyryl mitomycin C | 25 | 3.125 | 3.125 | 19.0 |
| 1a-crotonoyl mitomycin C | 12.5 | 1.563 | 0.782 | 35.5 |
| 1a-decanoyl mitomycin C | >50 | 0.782 | 12.5 | 67.5 |
| 1a-lauroyl mitomycin C | >50 | 0.391 | >50 | 44.5 |
| 1a-myristoyl mitomycin C | 1.563 | 0.391 | >50 | 45 |
| 1a-palmitoyl mitomycin C | 0.782 | 0.782 | >50 | 75 |
| 1a-stearoyl mitomycin C | >50 | >50 | >50 | 75 |
| 1a-oleoyl mitomycin C | 1.563 | 0.782 | >50 | 105 |
| 1a-ricinoleoyl mitomycin C | 0.782 | 0.391 | 0.782 | 60 |
| 1a-vaccenoyl mitomycin C | 3.125 | 0.782 | 50 | 105 |
| 1a-linoleoyl mitomycin C | 0.782 | 0.782 | 12.5 | 110 |
| 1a-linolenoyl mitomycin C | 1.563 | 0.782 | 6.25 | 95 |
| 1a-ercoyl mitomycin C | >50 | >50 | 50 | 125 |

As is apparent from the above Table 1, the new derivatives of mitomycin C of the present invention exhibit a strong antibacterial activity, particularly against Gram-positive bacteria. These compounds have much reduced toxicity as compared with mitomycin C ($LD_{50}$: 9.0 mg/kg).

The lipid-solubility of some of the present compounds is compared with that of mitomycin C. In determining the lipid-solubility, the distribution ratio of the compound in water and butanol (1:1) is used as the standard. The results are shown in Table 2 below.

TABLE 2

Distribution Ratio of mitomycin C and 1a-acyl derivatives of mitomycin C of the present invention.

| Compound | Distribution Ratio [in butanol/water (1:1) at 25° C] (butanol/water) |
|---|---|
| mitomycin C | 2.471 |
| 1a-acetyl mitomycin C | 3.749 |
| 1a-butyryl mitomycin C | 4.402 |
| 1a-decanoyl mitomycin C | 7.889 |
| 1a-linoleoyl mitomycin C | 9.665 |

As is apparent from Table 2, the lipid-solubility of the derivatives of mitomycin C of the present invention is remarkably improved. Even compared with known 1a-acyl derivatives such as an acetyl derivative of mitomycin C and a butyryl derivative of mitomycin C, 1a-acyl derivatives of mitomycin C of the present invention have considerably improved lipid-solubility.

Further, the anti-tumor activity of 1a-acyl derivatives of mitomycin C of the present invention against Sarcoma 180 solid tumor in mice is determined.

Small portions of Sarcoma 180 solid tumor are transplanted subcutaneously into male dd-strain mice of about 20 g body weight. To each of 10 mice transplanted with tumor, a solution containing one-sixth of the $LD_{50}$ value of the test compound is administered intraperitoneally once daily for 8 days starting on the day following the transplantation.

As a control, an equal volume of saline is injected in the same manner as above. On the 10th day after the transplantation, the mice are sacrificed and the weight of the tumor is measured. The ratio of average tumor weight of test animals to average tumor weight of control animals (T/C) is calculated. The results are shown in Table 3 below.

TABLE 3

Effect of 1a-acyl derivatives of mitomycin C in mice bearing Sarcoma 180 (solid)

| Substituent of 1a-position | Sarcoma 180 (T/C) |
|---|---|
| H (i.e. mitomycin C) | 0.35 |
| $COCH_3$ | 0.48 |
| $COCH_2CH_2CH_3$ | 0.59 |
| $COCH=CHCH_3$ | 0.53 |
| $CO(CH_2)_7CH=CH(CH_2)_7CH_3$ | 0.31 |
| $CO(CH_2)_7CH=CHCH_2CH(CH_2)_5CH_3$<br>$\quad\quad\quad\quad\quad\quad\quad\quad\quad\quad\quad$ \|<br>$\quad\quad\quad\quad\quad\quad\quad\quad\quad\quad\quad$ OH | 0.28 |
| $CO(CH_2)_9CH=CH(CH_2)_5CH_3$ | 0.34 |
| $CO(CH_2)_7CH=CHCH_2CH=CH(CH_2)_4CH_3$ | 0.35 |

From Table 3, it is apparent that 1a-higher aliphatic acyl derivatives of mitomycin C of the present invention have an anti-tumor activity against Sarcoma 180 solid tumor which is much superior to that of the well known 1a-lower aliphatic acyl derivatives of mitomycin C and the activity is comparative to or even higher than that of mitomycin C.

With such reduce toxicity, improved lipid-solubility and excellent anti-tumor activity, the 1a-higher aliphatic acyl derivatives of mitomycin C of the present invention are considered to be very useful compounds.

BRIEF DESCRIPTION OF DRAWINGS

The accompanying drawing illustrates infrared absorption spectrums for a number of the 1a-acyl derivatives of mitomycin C of the invention.

FIG. 4 shows the absorption spectrum of 1a-palmitoyl mitomycin C;

FIG. 5 shows the absorption spectrum of 1a-stearoyl mitomycin C;

FIG. 6 shows the absorption spectrum of 1a-oleoyl mitomycin C;

EXAMPLE 1

Figure 1:
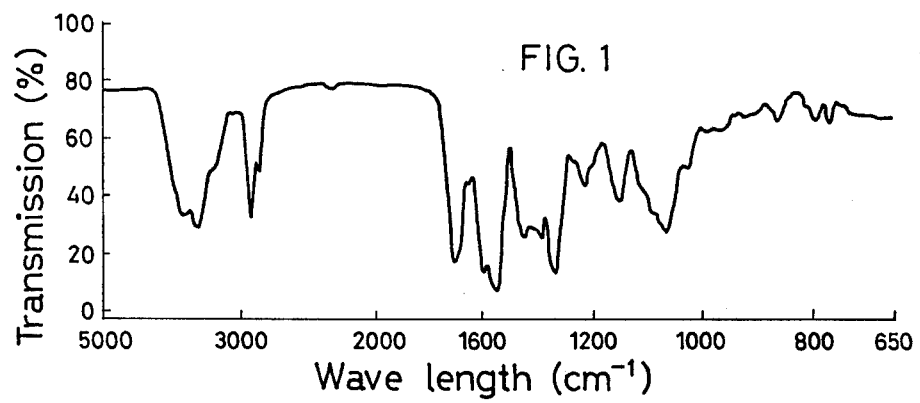
FIG. 1 shows the absorption spectrum of 1a-decanoyl mitomycin C.

Production of 1a-decanoyl mitomycin C 2,060 mg of dicyclohexylcarbodiimide and 1,720 mg of decanoic acid are added to 100 ml of methylene chloride. The mixture is stirred at 5° C. for 30 minutes. Then, to the mixutre is added 668 mg of mitomycin C and the mixture is stirred at room temperature for 15 hours. A white precipitate is formed and filtered off and the filtrate is concentrated under reduced pressure. The concentrated residue is subjected to silica gel column chromatography using a developer of acetone and chloroform (1:1). The eluate is concentrated to dryness under reduced pressure. 900 mg of crude 1a-decanoyl mitomycin C is obtained as a purple-colored powder in a 92% yield. Melting point: 140° to 142° C. The thus obtained product shows a higher Rf value than mitomycin C in silica gel thin layer chromatography using a developer of acetone and chloroform (1:1). FIG. 1 illustrates an infrared absorption spectrum of the product as KBr tablet.

EXAMPLE 2

Figure 2:
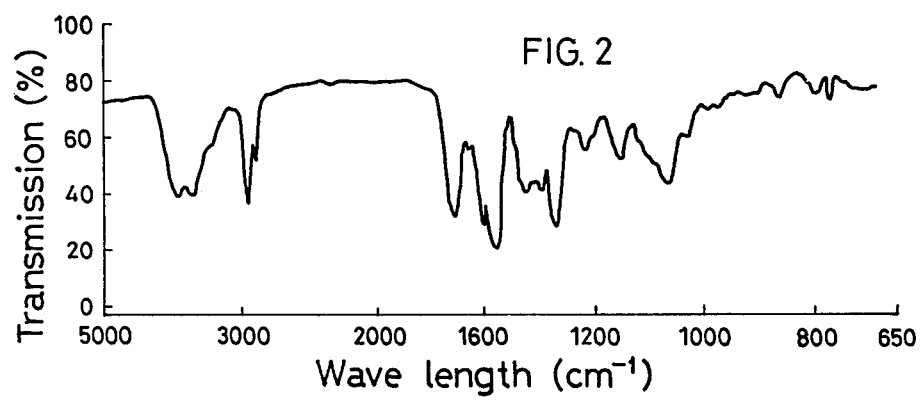
FIG. 2 shows the absorption spectrum of 1a-lauroyl mitomycin C.

Production of 1a-lauroyl mitomycin C 500 mg of mitomycin C and 5 ml of triethylamine are added to 50 ml of tetrahydrofuran. The mixture is cooled with ice. A solution of 2 ml of lauryl chloride in 100 ml of tetrahydrofuran is gradually added dropwise to the mixture over about 7 hours. After the completion of addition, the reaction mixture is filtered and the filtrate is concentrated under reduced pressure. The residue is treated in the same manner as described in Example 1. 500 mg of crude 1a-lauroyl mitomycin C is obtained as a purple-colored powder in a 65% yield. Melting point: 50° to 60° C. The thus obtained 1a-lauroyl mitomycin C shows a higher Rf value than mitomycin C in silica gel thin layer chromatography using a developer of acetone and chloroform (1:1). FIG. 2 illustrates an infrared absorption spectrum of the product as KBr tablet.

EXAMPLE 3

Figure 3:
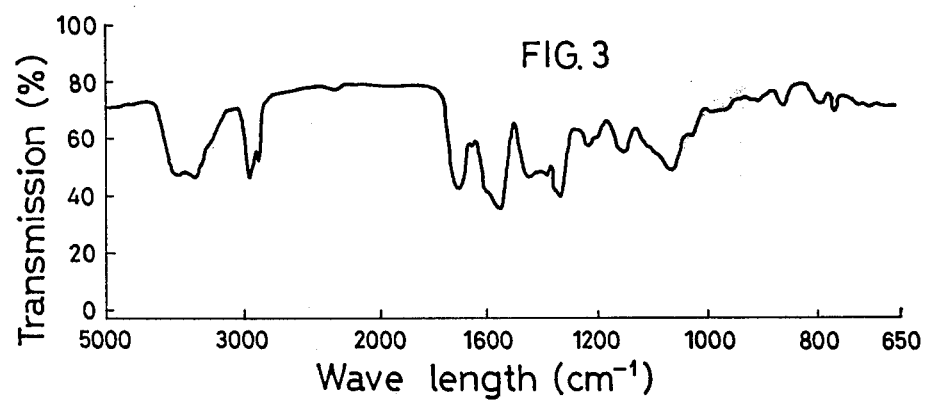
FIG. 3 shows the absorption spectrum of 1a-myristoyl mitomycin C.

Production of 1a-myristoyl mitomycin C 668 mg of mitomycin C and 5 g of sodium hydrogencarbonate are added to 50 ml of chloroform and the mixture is cooled with ice. A solution of 1 ml of myristyl bromide in 50 ml of dioxane is added dropwise to the mixture over about 10 hours. After the completion of addition, the reaction mixture is treated in the same manner as described in Example 2. 920 mg of crude 1a-myristoyl mitomycin C is obtained as a purple-colored powder in an 84.5% yield. Melting point: 65° to 75° C. The thus obtained 1a-myristoyl mitomycin C shows a higher Rf value than mitomycin C in silica gel thin layer chromatography using a developer of acetone and chloroform (1:1). FIG. 3 illustrates an infrared absorption spectrum of the product as KBr tablet.

EXAMPLE 4

Production of 1a-palmitoyl mitomycin C a. 2 g of palmitic acid anhydride and 668 mg of mitomycin C are added to 50 ml of pyridine and the mixture is stirred at room temperature for 15 hours. The resulting reaction mixture is subjected to extraction with ethyl acetate. The extract is washed with water. The layer of ethyl acetate is dried with anhydrous sodium sulfate and the dried matter is filtered. The filtrate is concentrated under reduced pressure. The residue is treated in the same manner as described in Example 1. 1 g of crude 1a-palmitoyl mitomycin C is obtained as a purple-colored powder in an 87% yield. Melting point: 63° to 73° C. The thus obtained 1a-palmitoyl mitomycin C shows a higher Rf value than mitomycin C in silica gel thin layer chromatography using a developer of acetone and chloroform (1:1). FIG. 4 illustrates an infrared absorption spectrum of the product as KBr tablet.

b. 1 g of potassium carbonate, 0.4 g of palmitic acid anhydride and 66.8 mg of mitomycin C are added to 10 ml of dimethylformamide and the mixture is stirred at room temperature for 7 hours. The reaction mixture is treated in the same manner as described in Example 4-(a) above and 82 mg of a purple-colored powder is obtained in a 71% yield. The silica gel thin layer chromatogram and the infrared absorption spectrum of the thus obtained compound are identical with those of the compound obtained in Example 4-(a) above.

Example 5

Production of 1a-stearoyl mitomycin C 1 g of methyl stearate, 0.5 g of hydrazine hydrate are added to 14 ml of ethanol and the mixture is stirred at room temperature for 15 hours. The resulting reaction mixture is concentrated under reduced pressure. To the residue is added 10 ml of water and cooled to 0° C. To the mixture are added 2 ml of acetic acid and then a solution of 1.4 g of sodium nitrite in 10 ml of water. The mixture is subjected to extraction with ether. The layer of ether is washed with water and dried with anhydrous magnesium sulfate and the magnesium sulfate is filtered off. The filtrate is concentrated under reduced pressure. To the residue are added 50 ml of tetrahydrofuran and 668 mg of mitomycin C and the mixture is stirred for 15 hours. After the completion of reaction, the reaction mixture is concentrated under reduced pressure and the residue is subjected to silica gel column chromatography in the same manner as in Example 1, whereby 430 mg of crude 1a-stearoyl mitomycin C is obtained as a purple-colored powder in a 36% yield. Melting point: 65° to 74° C. The thus obtained 1a-stearoyl mitomycin C shows a higher Rf value than mitomycin C in silica gel thin layer chromatography using a developer of acetone and chloroform (1:1). FIG. 5 illustrates an infrared absorption spectrum of the product as KBr tablet.

EXAMPLE 6

Production of 1a-oleoyl mitomycin C 565 mg of oleic acid and 204 mg of triethylamine are dissolved in a mixture of 5 ml of toluene and 5 ml of chloroform. The solution is cooled to −5° C. 241 mg of isovaleryl chloride is added thereto and stirred for 2 hours. Then, 668 mg of mitomycin C and 50 ml of chloroform are added thereto and the mixture is stirred at 10° C. for 15 hours. The reaction mixture is washed with water, dried with anhydrous sodium sulfate and filtered. The filtrate is concentrated under reduced pressure. The concentrate is purified by silica gel column chromatography in the same manner as in Example 1, whereby 420 mg of crude 1a-oleoyl mitomycin C is obtained as a purple-colored powder in a 35% yield. Melting point: 50° to 57° C. The thus obtained 1a-oleoyl mitomycin C shows a higher Rf value than mitomycin C in silica gel thin layer chromatography using a developer of acetone and chloroform (1:1). FIG. 6 illustrates an infrared absorption spectrum of the product as KBr tablet.

EXAMPLE 7

Figure 7:
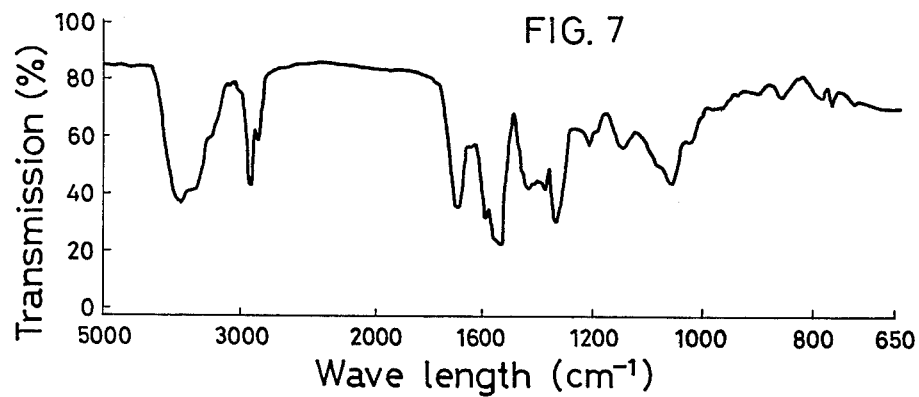
FIG. 7 shows the absorption spectrum of 1a-ricinoleoyl mitomycin C.

Production of 1a-ricinoleoyl mitomycin C 2,700 mg of ditolylcarbodiimide and 2,984 mg of ricinoleic acid are added to 100 ml of acetonitrile. The mixture is stirred for 30 minutes while cooling with ice. To the mixture is added 668 mg of mitomycin C. The mixture is stirred at room temperature for 15 hours, and treated in the same manner as in Example 1. 510 mg of crude 1a-ricinoleoyl mitomycin C is obtained as a purple-colored powder in a 41% yield. Melting point: 50° to 54° C. The thus obtained 1a-ricinoleoyl mitomycin C shows a higher Rf value than mitomycin C in silica gel thin layer chromatography using a developer of acetone and chloroform (1:1). FIG. 7 illustrates and infrared absorption spectrum of the product as KBr tablet.

EXAMPLE 8

Figure 8:
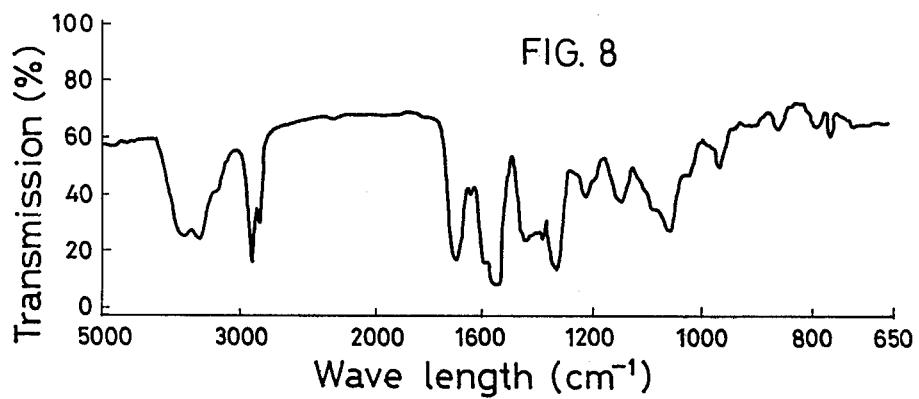
FIG. 8 shows the absorption spectrum of 1a-vaccenoyl mitomycin C.

Production of 1a-vaccenoyl mitomycin C 900 mg of p-nitrophenyl vaccenate and 668 mg of mitomycin C are added to 100 ml of chloroform. The mixture is stirred at room temperature for 20 hours and concentrated under reduced pressure. The residue is subjected to silica gel column chromatography in the same manner as in Example 1, whereby crude 1a-vaccenoyl mitomycin C is obtained as a purple-colored powder in a 68% yield. Melting point: 54° to 64° C. In silica gel thin layer chromatography using a developer of acetone and chloroform (1:1), the thus obtained 1a-vaccenoyl mitomycin C shows a higher Rf value than mitomycin C. FIG. 8 illustrates an infrared absorption spectrum of the product as KBr tablet.

EXAMPLE 9

Figure 9:
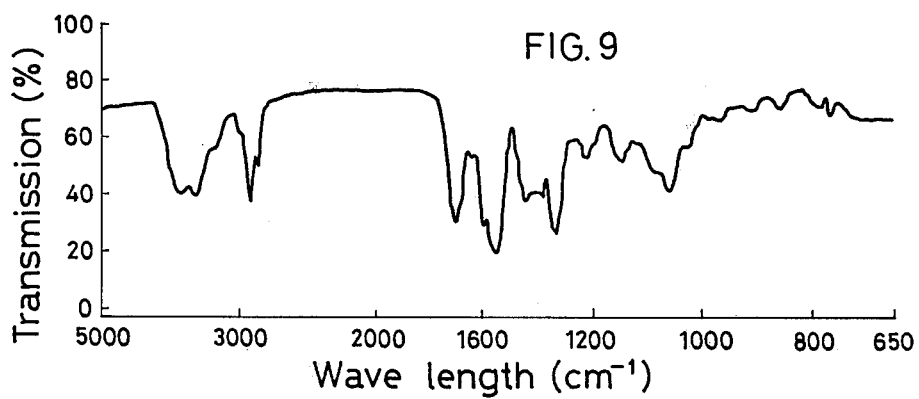
FIG. 9 shows the absorption spectrum of 1a-linoleoyl mitomycin C.

Production of la-linoleoyl mitomycin C (a) 1,260 mg of di-n-propylcarbodiimide and 2,804 mg of linoleic acid are added to 100 ml of ethyl acetate. The mixture is stirred for 30 minutes while cooling with ice. Then 668 mg of mitomycin C is added thereto, and stirred at room temperature for 15 hours. The reaction mixture is treated in the same manner as in Example 1. As a result, 970 mg of crude la-linoleoyl mitomycin C is obtained as a purple-colored powder in an 81% yield. Melting point: 75° C. to 85° C. The thus obtained la-linoleoyl mitomycin C shows a higher Rf value than mitomycin C in silica gel thin layer chromatography using a developer of acetone and chloroform (1:1). FIG. 9 illustrates an infrared absorption spectrum of la-linoleoyl mitomycin C as KBr tablet.

b. 126 mg of diisopropylcarbodiimide and 280 mg of linoleic acid are added to 10 ml of water. The mixture is stirred for 30 minutes while cooling with ice. Then 66.8 mg of mitomycin C is added thereto, and stirred at room temperature for 30 hours. The reaction mixture is subjected to extraction with ethyl acetate. The layer of ethyl acetate is dried with anhydrous sodium sulfate and filtered. The filtrate is concentrated under reduced pressure. The residue from the concentration is purified with silica gel column chromatography in the same manner as in Example 1. 73 mg of a purple-colored powder is obtained in a 61% yield. The silica gel thin layer chromatogram and the infrared absorption spectrum of the thus obtained compound are identical with those of the compound obtained in Example 9 -(a) above.

c. 206 mg of dicyclohexylcarbodiimide and 280 mg of linoleic acid are added to 10 ml of dimethylformamide. The mixture is stirred for 30 minutes while cooling with ice. 66.8 mg of mitomycin C is added thereto and the mixture is stirred at room temperature for 15 hours. Then the reaction mixture is treated in the same manner as in Example 1. 57 mg of a purple-colored powder is obtained in a 48% yield. The silica gel thin layer chromatogram and the infrared absorption spectrum of the thus obtained compound are identical with those of the compound obtained in Example 9-(a) above.

d. The same procedure as described in Example 9-(c) is repeated except for using 10 ml of pyridine in place of dimethylformamide. 21 mg of a purple-colored powder is obtained in an 18% yield. The silica gel thin layer chromatogram and the infrared absorption spectrum of the thus obtained compound are identical with those of the compound obtained in Example 9-(a).

e. The same procedure as described in Example 9-(c) is repeated except for using 10 ml of n-propanol in place of dimethylformamide. 44 mg of a purple-colored powder is obtained in a 37% yield. The silica gel thin layer chromatogram and the infrared absorption spectrum of the thus obtained compound are identical with those of the compound obtained in Example 9-(a).

f. The same procedure as described in Example 9-(c) is repeated except for using 10 ml of dioxane in place of dimethylformamide. 91 mg of a purple-colored powder is obtained in a 71% yield. The thus obtained compound coincides with that obtained in Example 9-(a) in the silica gel thin layer chromatogram and the infrared absorption spectrum.

g. The same procedure as described as described in Example 9-(c) is repeated except for using 10 ml of benzene in place of dimethylformamide. 36 mg of a purple-colored powder is obtained in a 30% yield. The thus obtained compound coincides with that obtained in Example 9-(a) in the silica gel thin layer chromatogram and the infrared absorption spectrum.

h. The same procedure as described in Example 9-(c) is repeated except for using 10 ml of acetone in place of dimethylformamide. 58 mg of a purple-colored powder is obtained in a 48% yield. The thus obtained compound coincides with that obtained in Example 9-(a) in the silica gel thin layer chromatogram and the infrared absorption spectrum.

EXAMPLE 10

Figure 10:
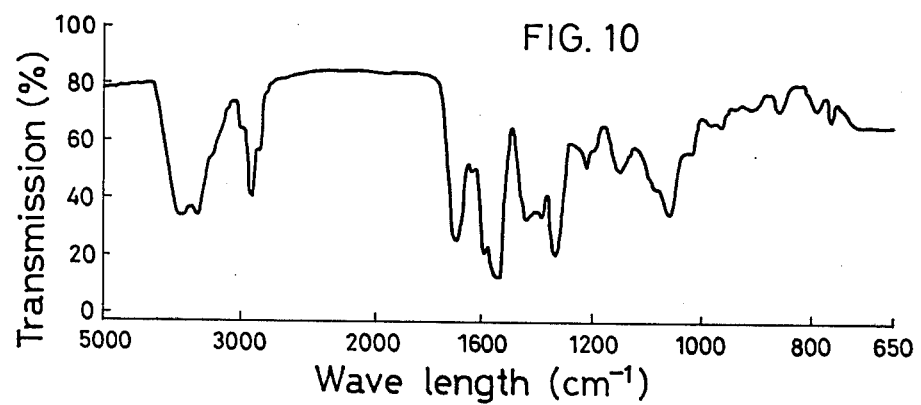
FIG. 10 shows the absorption spectrum of 1a-linolenoyl mitomycin C.

Production of la-linolenoyl mitomycin C 840 mg of N,N-diethyl cyanamide and 2,784 mg of linolenic acid are added to 100 ml of tetrahydrofuran. The mixture is stirred at room temperature for 30 minutes. 668 mg of mitomycin C is added thereto and the mixture is stirred at room temperature for 15 hours. The reaction mixture is subjected to the same procedure as described in Example 1. 1,020 mg of a purple-colored powder is obtained in an 85% yield. Melting point: 83° to 90° C. In silica gel thin layer chromatography using a developer of acetone and chloroform (1:1), the thus obtained product shows a higher Rf value than mitomycin C. FIG. 10 illustrates an infrared absorption spectrum of the product as KBr tablet.

EXAMPLE 11

Figure 11:
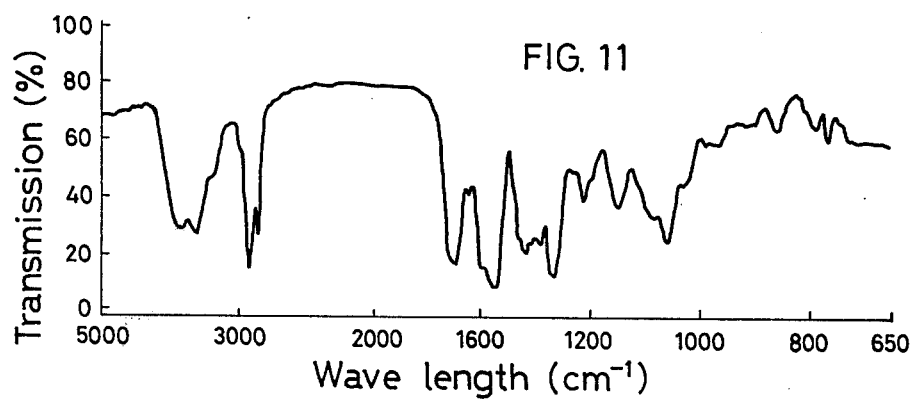
FIG. 11 shows the absorption spectrum of 1a-ercoyl mitomycin C.

Production of la-ercoyl mitomycin C 5 g of sodium hydrogencarbonate and 668 mg of mitomycin C are added to 50 ml of benzene. A solution of 1 ml of erucyl chloride in 50 ml of tetrahydrofuran is gradually added dropwise to the mixture over 8 hours. Then the same procedure as described in Example 2 is carried out. 1,160 mg of crude la-ercoyl mitomycin C is obtained as a purple-colored powder in an 88% yield. In silica gel thin layer chromatography using a developer of acetone and chloroform (1:1), the thus obtained product shows a higher Rf value than mitomycin C. FIG. 11 illustrates an infrared absorption spectrum of the product as KBr tablet.

What is claimed is:
1. la-oleoyl mitomycin C.
2. la-ricinoleoyl mitomycin C.
3. la-vaccenoyl mitomycin C.
4. la-linoleoyl mitomycin C.

* * * * *